US009272067B2

(12) United States Patent
Lombardo

(10) Patent No.: US 9,272,067 B2
(45) Date of Patent: Mar. 1, 2016

(54) SOLID FILM, RAPIDLY DISSOLVABLE IN LIQUIDS

(75) Inventor: Paola Lombardo, Costa Mezzate (IT)

(73) Assignee: BIOFARMITALIA S.p.A, Milan (IT)

( * ) Notice: Subject to any disclaimer, the term of this patent is extended or adjusted under 35 U.S.C. 154(b) by 580 days.

(21) Appl. No.: 12/508,044

(22) Filed: Jul. 23, 2009

(65) Prior Publication Data

US 2010/0029790 A1    Feb. 4, 2010

(30) Foreign Application Priority Data

Aug. 4, 2008  (IT) .............. MI2008A1450

(51) Int. Cl.

| | | |
|---|---|---|
| *A61K 47/00* | (2006.01) | |
| *A61L 15/28* | (2006.01) | |
| *A23L 1/22* | (2006.01) | |
| *A61K 9/00* | (2006.01) | |
| *A61K 9/70* | (2006.01) | |
| *A61L 15/32* | (2006.01) | |
| *A61L 15/44* | (2006.01) | |

(52) U.S. Cl.
CPC .............. *A61L 15/28* (2013.01); *A23L 1/2205* (2013.01); *A61K 9/006* (2013.01); *A61K 9/0056* (2013.01); *A61K 9/7007* (2013.01); *A61L 15/32* (2013.01); *A61L 15/44* (2013.01); *A61L 2300/604* (2013.01)

(58) Field of Classification Search
USPC ........................................... 514/779
See application file for complete search history.

(56) References Cited

U.S. PATENT DOCUMENTS

| | | | |
|---|---|---|---|
| 3,582,357 A  * | 6/1971 | Katz .............................. | 426/564 |
| 6,656,493 B2 * | 12/2003 | Dzija et al. .................... | 424/439 |
| 2003/0054039 A1 | 3/2003 | Zyck et al. | |
| 2004/0115137 A1* | 6/2004 | Verrall et al. ................... | 424/48 |
| 2005/0003048 A1* | 1/2005 | Pearce et al. ................... | 426/74 |
| 2005/0075432 A1 | 4/2005 | Verrall et al. | |
| 2005/0089548 A1* | 4/2005 | Virgalitto et al. ............. | 424/440 |
| 2006/0147393 A1* | 7/2006 | Macchi ............................ | 424/49 |
| 2008/0063682 A1* | 3/2008 | Cashman et al. ............. | 424/423 |
| 2008/0220029 A1* | 9/2008 | Ng et al. ........................ | 424/401 |

FOREIGN PATENT DOCUMENTS

EP          1 738 656 A1     1/2007

* cited by examiner

*Primary Examiner* — Rei-Tsang Shiao
(74) *Attorney, Agent, or Firm* — Oblon, McClelland, Maier & Neustadt, L.L.P.

(57) ABSTRACT

A solid film rapidly dissolvable in liquids, in particular biological liquids, to release pharmaceutical, cosmetic and nutrient substances. The solid film is also soluble in biological organic liquids to protect wounds of the human body by releasing cicatrizing, disinfectant and cosmetic substances. The film can also be used to release flavoring substances directly onto moist nutrient products.

22 Claims, No Drawings

SOLID FILM, RAPIDLY DISSOLVABLE IN LIQUIDS

CROSS-REFERENCE TO RELATED APPLICATIONS

This application claims the benefit of Italian application MI2008A 001450 filed Aug. 4, 2008.

The present invention relates to a solid film rapidly dissolvable in liquids usable for pharmaceutical, cosmetic treatment or alimentation of the human body, or for releasing aromatic and similar substances onto products intended for human nutrition. The film can also be applied in the veterinary field.

Of all administration methods, oral drug administration is probably that preferred both by the patient and by the clinicians. However, direct oral drug administration has certain drawbacks, such as hepatic first pass metabolism and enzymatic degradation within the gastrointestinal tract, which hinders this type of administration for certain drug classes, especially peptides and proteins. Consequently, other absorbent mucosas are considered as potential drug administration sites.

Transmucosal routes (in particular rectal, vaginal, ocular and oral cavity administration) offer various advantages over the oral route. These include the ability to bypass the hepatic first pass, avoid pre-systemic elimination in the gastrointestinal tract and, for particular drugs, the presence of better enzymatic flora for absorption. Although the rectal, vaginal and ocular mucosa offer some advantages, the poor acceptability by the patient means that these are useful only for local administration rather than systemic administration. In contrast, the oral cavity is well accepted by the patient, its mucosa is relatively permeable, possesses a rich blood supply, is strong and shows a short recovery time after stress or damage. Moreover, the lack of Langerhans cells makes the oral mucosa tolerant to potential allergens. These factors mean that the oral cavity is considered a very interesting site for systemic release of drugs and cosmetic and alimentary products.

In general the oral mucosa represents a sort of intermediate epithelium between the epidermis and the intestinal mucosa and enables rapid and effective treatment of toothache, bacterial infections and mycosis, aphthas and dental stomatitis. The aforestated indicates that the oral mucosa has become an important administration route, as a result of which various formulations have been developed. These include: adhesive tablets, gels, ointments, patches and more recently solid films. Polymeric films were widely used as formulations to cover tablets such as to protect them from extreme environments, improve their appearance, mask unpleasant tastes and control the release of the drug (Peh, K K and Wong, J. Pharm. Pharmaceut. Sci. 2(2):53-61, 1999). Development of the technology for producing edible films is becoming an important challenge for the future, and its use is proving to extend beyond the aforestated functions. In this respect, buccal films are becoming preferred to adhesive tablets in terms of comfort and flexibility, they can easily protect the surface of wounds such as to reduce pain, and can also heal oral ailments more effectively (Peh, 1999). Moreover, edible films are more suitable for the elderly and children, who have difficulty in self-administering a suitable drug dose. The use of these devices reduces the risk of suffocation and increases patient compliance. The term "edible" applies to materials of food grade approved by the regulatory authorities for use in pharmaceutical and alimentary applications (Augello, U.S. Pat. No. 6,723,342).

An object of the present invention is to provide a solid edible film which can be used as a vehicle for pharmaceutical, cosmetic and/or herbal (e.g. food supplement) active principles. The principle need is to achieve a solid film with a simple structure such as to enable active products to be inserted in percentages sufficient to develop their activity.

The main characteristics of the solid film to be sought are the following:

Operativity (simple, rapid preparation with consequent energy saving);

Standardization of spreading parameters (temperature, ventilation, speed, etc.) independently of the active product or products inserted into the film;

Film flexibility and plasticity (a fragile film is difficult to manipulate and to undergo all the production steps, for example punching);

Planarity (a film which tends to roll up after the spreading step cannot be subjected to the subsequent production steps);

Ability to insert powdered active products into the film (inserting these active products often renders the film fragile);

Homogeneity (a film which tends to incorporate air, besides being fragile, does not enable the active product or products inserted into the film to be homogeneously distributed).

To attain the aforesaid objects, a solid film rapidly dissolvable in liquids (in particular in contact with the saliva or human organic liquids in general) has been provided which is able to release in a very short time the active product or products incorporated therein, either systemically, in particular by absorption through the oral mucosa, or topically on the site of application, which can again be the oral mucosa or other mucosas, or the skin.

It has also been discovered that this film could, in the same simple and effective manner, incorporate and release cosmetic and nutrient products, aromatic substances, cicatrizants and the like.

The present invention hence provides a solid film rapidly dissolvable in liquids, for treating the human body or animals and for alimentary use, characterised by comprising between 25% and 60% of sodium alginate, between 0.1% and 20% of microcrystalline cellulose, between 0.1% and 25% of vegetable proteins (for example from vegetables of the legume family or from cereals), the percentages being by weight on the weight of the finished solid film, and by comprising water in a quantity such that its activity ($A_w$), i.e. the ratio of the vapour pressure of the water present in a mixture, in particular in the solid film, to the vapour pressure of pure water at the same temperature, is between 0.1 and 0.3, the solid film having a thickness between 60 and 150 µm.

According to a preferred aspect, the aforesaid film comprises at least one substance chosen from the group consisting of emulsifying products, emulsifiers/texturizers, plasticizing/wetting agents, filmogens, aromatizers, products with pharmacological activity, with cosmetic activity and products with alimentary properties. Preferably, said emulsifying products and emulsifiers/texturizers are chosen from the group consisting of polyoxyethylene derivatives (for example polysorbate 60, polysorbate 80), natural gums (for example carob seed flour, acacia gum), natural emulsifiers (for example gelatine), cellulose derivatives (for example carboxymethylcellulose, methylcellulose) and starches (for example maize and potatoes). Preferably, said agents are chosen from the group consisting of polyols (for example glycerin, sorbitol, propylene glycol) and the ester of acetic acid with glycerol (glyceryl triacetate). Preferably, said filmogenic substances are chosen from the group consisting of glycosaminoglycans known also as GAGs, mucopolysaccharides (for example hyaluronic acid) and water-soluble polysaccharides such as pullulan.

The aforesaid film has preferably a solubilization time between 10 and 20 seconds.

Sodium alginate is a well known substance with filmogenic and emulsifying properties, widely used in the pharmaceutical and alimentary industries, and is a water-soluble salt of aginic acid, a non-toxic polysaccharide present in all species of brown algae. It is preferably present in a quantity from 30% to 50% by weight of the solid film.

Microcrystalline cellulose has a thickening/stabilizing and emulsifying function and is a purified and partially depolymerized cellulose in the form of an odourless, tasteless white crystalline powder. The characteristics and methods of preparation of microcrystalline cellulose are well known.

Microcrystalline cellulose is present in the finished film in a quantity by weight (on the total weight) from 0.1% to 20% after evaporating the solvents, and preferably from 2.5% to 11%.

The vegetable proteins used in the films of the present invention can be, for example, those commonly used as emulsifiers/texturizers in the alimentary product sector, breakfast cereals and confectionery, products made by a process known as extrusion. Inserting vegetable proteins, preferably from vegetables of the legume family or from cereals, and more preferably from peas, helps to attain an $A_w$ value between 0.1 and 0.3, enabling the product to be preserved without the need to dry it such as to deteriorate the film mechanical properties, in particular its flexibility, and without inserting substances of other types which could be undesirable. These vegetable proteins are present in quantities from 0.1% to 25% on the weight of the finished product after solvent evaporation, preferably from 5% to 15%.

The solid preparations of the present invention preferably comprise at least one further component chosen from the following groups:

Emulsifying substances chosen from the group comprising polyoxyethylene derivatives such as polysorbate 60 and polysorbate 80, in a quantity from 0% to 20% by weight on the finished product after solvent evaporation, preferably from 5% to 12%.

Wetting/plasticizing substances pertaining to the polyol family (this refers to chemical compounds containing a plurality of hydroxyl groups) such as glycerin and sorbitol, in a quantity from 0% to 50% by weight on the finished product after solvent evaporation, preferably from 15% to 45%.

Emulsifiers/texturizers pertaining to the starch family. Starches play a likewise important role in alimentary technology because of their physico-chemical and functional properties. They are used as thickening agents to increase the viscosity of sauces and soups, as gel or emulsion stabilizing agents, as binding agents, and as filling agents by virtue of their capacity to bind water. In the food industry the five main sources of starch are maize, potatoes, rice, tapioca and wheat. These substances can be present in quantities from 0% to 5% on the weight of the finished product after solvent evaporation, preferably from 1% to 4%.

The solid compositions obtained according to the present invention can be produced in the form of solid films of thickness between 60 and 150 μm and are able to carry active principles normally used in the pharmaceutical, cosmetic and food supplement field.

Said solid films, having good dimensional stability, can be punched or cut into the most suitable formats for their use (pharmaceutical/food supplement).

The aforesaid solid compositions can be obtained by the following method: the aforesaid compositions, selected on the basis of the characteristics to be imparted to the finished product, are dispersed progressively in a mixer containing water preheated between 50° C. and 70° C.; the mix is maintained under agitation until it is homogeneous.

The sodium alginate and microcrystalline cellulose are then trickled in, while slowly mixing to prevent lump formation.

After cooling under slow agitation (to about 30° C.) and checking the organoleptic characteristics of the product, the mass obtained is spread by a doctor blade as a film of thickness between 180 and 270 μm onto a silicone coated surface of a support belt which is made to pass through a ventilated tunnel oven, having successive heating stations with temperatures increasing to 120° C., and with the last station at the lowest temperature, between 60° C. and 90° C.; at the oven exit a solid film of thickness between 60 and 150 μm separates from the support belt and is cooled to ambient temperature, then punched into the required shape and size and divided into unit portions.

The unit portions obtained can then be inserted into final packaging from which they can be withdrawn at the time of use.

To optimize the aforesaid process, the heated tunnel oven must have at least one drying station at variable temperature, better if four successive stations, the first of which is heated to a temperature between 60° C. and 80° C., the second and third to a temperature between 70° C. and 90° C., and the fourth between 60° C. and 80° C.

The characteristics of the solid compositions of the present invention, and their production method, will be more apparent from the following description of some non-limiting embodiments.

EXAMPLE I

Production of a Solid Film with Cicatrizing Filmogenic Action for Small Skin Wounds To prepare a composition (in the form of a solid film) according to the present invention, the following components are used:

| COMPONENT | FUNCTION | COMPONENT QUANTITY |
|---|---|---|
| 1) Water | Solvent | 81.6 Kg |
| 2) Sodium Alginate | Filmogen/Emulsifier | 8.7 Kg |
| 3) Microcrystalline Cellulose | Thickener/Stabilizer | 1.7 Kg |
| 4) Vegetable Proteins | Emulsifiers/Texturizers | 1.0 Kg |
| 5) Polysorbate - 80 | Emulsifier | 2.0 Kg |
| 6) Glycerin | Wetting agent/Plasticizer | 5.0 Kg |

Operating Method

The following steps are carried out in succession:

A) Components 5) (polysorbate 80) and 6) (glycerin) are dispersed under agitation in a mixer containing water 1) preheated to between 50° C. and 70° C.; agitation is continued until completely dissolved.

B) Components 2) (sodium alginate), 3) (microcrystalline cellulose) and 4) (vegetable proteins) are trickled in and agitated for 30 min with slow agitation until completely dispersed and the gel is homogeneous.

C) Slow cooling is commenced under agitation to 25° C.; agitation is continued until homogeneous.

D) Still under agitation, using a peristaltic pump, the mixture obtained is fed onto a doctor blade heated to 30° C. and then filmed to 200 μm thickness on a belt support of silicon-coated polyester. During film formation a ventilated tunnel oven is used provided with four successive heating stations having the following temperatures respectively: 70/80/80/70° C.

E) At the oven exit a film of 80 μm thickness (following water evaporation) automatically separates from the polyester support.

F) The film is punched into rectangles of dimensions 3×2 cm using a roller punch.

G) these rectangles are automatically inserted into a sealed container acting as a dispensing mechanism for the solid composition.

Characteristics of the Finished Solid Film

Weight of one unit (dimensions 3×2 cm): 47 mg

Thickness: 80 μm $A_w$ (water activity, i.e. the ratio of vapour pressure of the water present in the composition and the pressure of pure water at the same temperature): 0.3

| | |
|---|---|
| sodium alginate | 47.29% |
| microcrystalline cellulose | 9.24% |
| vegetable proteins | 5.43% |
| polysorbate 80 | 10.87% |
| glycerin | 27.17% |

(the percentages are by weight on the total weight of the finished solid film).

The film obtained is punched into sheets of about 6 cm² to give films which are inserted into a plastic container able to contain at least ten. This container is prepared for sale by suitable labelling and closure.

The product formed in this manner is particularly useful for small wounds, in that when the alginate and the microcellulose come into contact with the small wound exudates they dissolve to form a sort of gel, which maintains the wound occluded, so promoting its cicatrization.

EXAMPLE 2

Production of a Solid Film with Cicatrizing Filmogenic Action for Treating Aphthas To prepare a composition (in the form of a solid film) according to the present invention, the following components are used:

| COMPONENT | FUNCTION | COMPONENT QUANTITY |
|---|---|---|
| 1) Water | Solvent | 79.2 Kg |
| 2) Sodium Alginate | Filmogen/Emulsifier | 7.0 Kg |
| 3) Microcrystalline Cellulose | Thickener/Stabilizer | 0.5 Kg |
| 4) Vegetable Proteins | Emulsifiers/Texturizers | 2.0 Kg |
| 5) Polysorbate - 80 | Emulsifier | 2.0 Kg |
| 6) Glycerin | Wetting agent/Plasticizer | 5.0 Kg |
| 7) Sorbitol 70% | Wetting agent/Plasticizer | 2.5 Kg |
| 8) Mint Flavour | Flavouring | 1.0 Kg |
| 9) Hyaluronic acid | Filmogen/MW 1,200,000 | 0.8 Kg |

Operating Method

The following steps are carried out in succession:

A) Components 5) (polysorbate 80), 6) (glycerin), 7) (Sorbitol 70%) and 9) (Hyaluronic acid) are dispersed under agitation in a mixer containing water 1) preheated to between 50° C. and 70° C.; agitation is continued until a clear lump-free gel is obtained (verify complete dispersion of component 9) (hyaluronic acid).

B) Components 2) (sodium alginate), 3) (microcrystalline cellulose) and 4) (vegetable proteins) are trickled in and agitated for 30 min with slow agitation until dispersion is complete and the gel is homogeneous.

C) Slow cooling is commenced under agitation to 25° C., then component 8) (flavour) is added; agitation is continued until homogeneous.

D) Still under agitation, using a peristaltic pump, the mixture obtained is fed onto a doctor blade heated to 30° C. and then filmed to 200 μm thickness on a belt support of silicon-coated polyester. During film formation a ventilated tunnel oven is used provided with four successive heating stations having the following temperatures respectively: 65/70/75/80° C.

E) At the oven exit a film of 67 μm thickness (following water evaporation) spontaneously separates from the polyester support.

F) The film is punched into rectangles of dimensions 3×2 cm using a roller punch.

G) These rectangles are automatically inserted into a sealed container acting as a dispensing mechanism for the solid composition.

Characteristics of the Finished Solid Film

Weight of one unit (dimensions 3×2 cm): 45 mg

Thickness: 67 μm $A_w$ (water activity, i.e. the ratio of vapour pressure of the water present in the composition and the pressure of pure water at the same temperature): 0.1

| | |
|---|---|
| sodium alginate | 34.92% |
| microcrystalline cellulose | 2.50% |
| vegetable proteins | 9.97% |
| polysorbate 80 | 9.97% |
| glycerin | 24.94% |
| sorbitol 70% | 8.73% |
| mint flavour | 4.98% |
| hyaluronic acid | 3.99% |

(the percentages are by weight on the total weight of the finished solid film)

The film obtained is punched into sheets of about 6 cm² to give films which are inserted into a plastic container able to contain at least ten sheets. This container is prepared for sale by suitable labelling and closure.

The product thus made is particularly useful for mouth infections, in that when the alginate and the microcellulose, but in particular the hyaluronic acid, come into contact with the mouth mucosa they structure to form a film which forms a barrier to aphtha infection, so rapidly promoting healing.

EXAMPLE 3

Production of a Solid Film Containing Melatonin

To prepare a composition (in the form of a solid film) according to the present invention, the following components are used:

| COMPONENT | FUNCTION | COMPONENT QUANTITY |
|---|---|---|
| 1) Water | Solvent | 78.00 Kg |
| 2) Sodium Alginate | Filmogen/Emulsifier | 9.0 Kg |
| 3) Microcrystalline Cellulose | Thickener/Stabilizer | 2.0 Kg |
| 4) Vegetable Proteins | Emulsifiers/Texturizers | 2.5 Kg |
| 5) Polysorbate - 60 | Emulsifier | 2.0 Kg |
| 6) Glycerin | Wetting agent/Plasticizer | 1.0 Kg |
| 7) Sorbitol 70% | Wetting agent/Plasticizer | 3.0 Kg |
| 8) Melatonin | Activant | 2.5 Kg |

Operating Method
A) Components 5) (polysorbate 60), 6) (glycerin) and 7) (Sorbitol 70%) are dispersed under agitation in a mixer containing water 1) preheated to between 50° C. and 70° C.; agitation is continued until completely dissolved.
B) Components 2) (sodium alginate), 3) (microcrystalline cellulose), 4) (vegetable proteins) and 8) (melatonin) are trickled in and agitated for 30 min with slow agitation until completely dispersed and the gel is homogeneous.
C) Slow cooling is commenced under agitation to 25° C.; agitation is continued until homogeneous.
D) Still under agitation, using a peristaltic pump the mixture obtained is fed onto a doctor blade heated to 30° C. and then filmed to 200 µm thickness on a belt support of silicon-coated polyester. During film formation a ventilated tunnel oven is used provided with four successive heating stations having the following temperatures respectively: 60/70/70/80° C.
E) At the oven exit a film of 70 µm thickness (following water evaporation) spontaneously separates from the polyester support.
F) The film is punched into rectangles of dimensions 3×2 cm using a roller punch.
G) These rectangles are automatically inserted into a sealed container acting as a dispensing mechanism for the solid composition.
Characteristics of the Finished Solid Film
Weight of one unit (dimensions 3×2 cm): 40 mg
Thickness: 70 µm
$A_w$ (water activity, i.e. the ratio of vapour pressure of the water present in the composition and the pressure of pure water at the same temperature): 0.2

| | |
|---|---|
| sodium alginate | 42.68% |
| microcrystalline cellulose | 9.47% |
| vegetable proteins | 11.84% |
| polysorbate 60 | 9.48% |
| glycerin | 4.74% |
| sorbitol 70% | 9.95% |
| melatonin | 11.84% |

(the percentages are by weight on the total weight of the finished product).

The film obtained is punched into sheets of about 6 cm² to give devices which are inserted into a plastic container able to contain at least ten of these devices. This container is prepared for sale by suitable labelling and closure.

The product thus made is particularly useful for rapid administration of melatonin, a natural promoter of cerebral relaxation and hence of sleep. The effectiveness of rapid administration by buccal absorption ensures an immediate effect, particularly useful for the initial stage of sleep, in contrast to that which takes place with tablet or operculum, which has to be digested by the gastric walls, requiring much longer times.

EXAMPLE 4

Production of a Flavoured Solid Film

To prepare a composition (in the form of a solid film) according to the present invention, the following components are used:

| COMPONENT | FUNCTION | COMPONENT QUANTITY |
|---|---|---|
| 1) Water | Solvent | 79.5 Kg |
| 2) Sodium Alginate | Filmogen/Emulsifier | 6.0 Kg |
| 3) Microcrystalline Cellulose | Thickener/Stabilizer | 1.5 Kg |
| 4) Vegetable Proteins | Emulsifiers/Texturizers | 3.0 Kg |
| 5) Polysorbate - 80 | Emulsifier | 1.0 Kg |
| 6) Maize starch | Texturizer | 0.5 Kg |
| 7) Glycerin | Wetting agent/Plasticizer | 5.0 Kg |
| 8) Sorbitol 70% | Wetting agent/Plasticizer | 2.5 Kg |
| 9) Saffron tincture | Flavouring | 1.0 Kg |

Operating Method
The following steps are carried out in succession:
A) Components 5) (polysorbate 80), 7) (glycerin) and 8) (Sorbitol 70%) are dispersed under agitation in a mixer containing water 1) preheated to between 50° C. and 70° C.; agitation is continued until completely dissolved.
B) Components 2) (sodium alginate), 3) (microcrystalline cellulose), 4) (vegetable proteins) and 6) (maize starch) are trickled in and agitated for 30 min with slow agitation until dispersion is complete and the gel is homogeneous.
C) Slow cooling is commenced under agitation to 25° C., then component 9) (flavouring) is added; agitation is continued until homogeneous.
D) Still under agitation, using a peristaltic pump, the mixture obtained is fed onto a doctor blade heated to 30° C. and then filmed to 200 µm thickness on a belt support of silicon-coated polyester. During film formation a ventilated tunnel oven is used provided with four successive heating stations having the following temperatures respectively: 60/70/70/80° C.
E) At the oven exit a film of 75 µm thickness (following water evaporation) spontaneously separates from the polyester support.
F) The film is punched into rectangles of dimensions 3×2 cm, using a roller punch.
G) These rectangles are automatically inserted into a sealed container, acting as a dispensing mechanism for the solid composition.
Characteristics of the Solid Device Obtained
Weight of one unit (dimensions 3×2 cm): 50 mg
Thickness: 80 µm
$A_w$ (water activity, i.e. the ratio of vapour pressure of the water present in the composition and the pressure of pure water at the same temperature): 0.3

| | |
|---|---|
| sodium alginate | 30.39% |
| microcrystalline cellulose | 7.59% |
| polysorbate 80 | 5.06% |
| glycerin | 25.32% |
| sorbitol 70% | 8.86% |
| vegetable proteins | 15.19% |
| maize starch | 2.53% |
| saffron tincture | 5.06% |

(the percentages are by weight on the total weight of the finished product)

The film obtained is punched into sheets of about 6 cm² to give devices which are inserted into a plastic container able to contain at least ten of these devices. This container is prepared for sale by suitable labelling and closure.

The devices thus made are particularly useful for flavouring food dishes and culinary preparations, and the dissolution rapidity of the film ensures ready and adequate dispersion of flavour throughout the dish. Larger dimension films can be made to totally cover a prepared food or one to be prepared, to better exalt its flavour.

EXAMPLE 5

Production of a Pharmaceutical Solid Film Containing an Antipropulsive

To prepare a composition (in the form of a solid film) according to the present invention, the following components are used:

| COMPONENT | FUNCTION | COMPONENT QUANTITY |
|---|---|---|
| 1) Water | Solvent | 65.90 Kg |
| 2) Sodium Alginate | Filmogen/Emulsifier | 8.7 Kg |
| 3) Microcrystalline Cellulose | Thickener/Stabilizer | 1.7 Kg |
| 4) Vegetable Proteins | Emulsifiers/Texturizers | 3.0 Kg |
| 5) Polysorbate - 80 | Emulsifier | 2.0 Kg |
| 6) Glycerin | Wetting agent/Plasticizer | 5.0 Kg |
| 7) Sorbitol 70% | Wetting agent/Plasticizer | 2.5 Kg |
| 8) Ethyl Alcohol | Solvent | 1.0 Kg |
| 9) Loperamide Hydrochloride | Activant | 1.2 Kg |

Operating Method
The following steps are carried out in succession:
A) Components 5) (polysorbate 80), 6) (glycerin) and 7) (Sorbitol 70%) are dispersed under agitation in a mixer containing water 1) preheated to between 50° C. and 70° C.; agitation is continued until completely dissolved.
B) Components 2) (sodium alginate), 3) (microcrystalline cellulose) and 4) (vegetable proteins) are trickled in and agitated for 30 min with slow agitation until dispersion is complete and the gel is homogeneous.
C) Slow cooling is commenced under agitation to 25° C., then the mixture formed by the component 8) (ethyl alcohol) plus 9) (loperamide hydrochloride) is added; agitation is continued until homogeneous.
D) Still under agitation, using a peristaltic pump the mixture obtained is fed onto a doctor blade heated to 30° C. and then filmed to 200 μm thickness on a belt support of silicon-coated polyester. During film formation a ventilated tunnel oven is used provided with four successive heating stations having the following temperatures respectively: 70/80/80/70° C.
E) At the oven exit, a film of 65 μm thickness (following water evaporation) spontaneously separates from the polyester support.
F) The film is punched into rectangles of dimensions 3×2 cm using a roller punch.
G) These rectangles form devices which are automatically inserted into a sealed container acting as a dispensing mechanism for the solid composition.
Characteristics of the Finished Solid Film
Weight of one unit (dimensions 3×2 cm): 40 mg
Thickness: 65 μm
$A_w$ (water activity, i.e. the ratio of vapour pressure of the water present in the composition and the pressure of pure water at the same temperature): 0.3

| | |
|---|---|
| sodium alginate | 37.28% |
| microcrystalline cellulose | 7.26% |
| polysorbate 80 | 8.57% |
| glycerin | 21.41% |
| sorbitol 70% | 7.49% |
| vegetable proteins | 12.85% |
| loperamide hydrochloride | 5.14% |

(the percentages are by weight on the total weight of the finished product).

The film obtained is punched into sheets of about 6 cm² to give devices which, by known processes, are inserted into and sealed within envelopes able to provide an adequate barrier against light, moisture and oxygen.

The film thus made in this manner is particularly useful in the case of sudden diarrhoea attacks, in that the rapid sublingual absorption, due to the rapidity with which the matrix dissolves in the mouth to immediately release the drug, allows it to act quickly.

The invention claimed is:

1. A solid film rapidly dissolvable in liquids and configured to have cicatizing filmogenic action for treating a small wound and/or an aphtha, comprising 25% and 60% of sodium alginate, 0.1% and 20% of microcrystalline cellulose, 0.1% and 25% of a vegetable protein, 5 to 12% polysorbate 60 or polysorbate 80, 15 to 45% of glycerin, sorbitol, or a combination thereof, the percentages being by weight on the weight of the finished solid film, and water, wherein the vegetable protein yields a water activity ($A_w$) of the solid film of between 0.1 and 0.3 and is the only preservation of the solid film and wherein the solid film is made by a process that comprises forming a film in a ventilated tunnel oven comprising four successive heating stations with a first heating station having a temperature of 60 to 80° C., a second heating station having a temperature of 70 to 90° C., a third heating station having a temperature of 70 to 90° C., and a fourth heating station having a temperature of 60 to 80° C.

2. The film as claimed in claim 1, having a dissolution time between 10 and 20 seconds.

3. The film as claimed in claim 1, further comprising at least one substance selected from the group consisting of an emulsifying product, an emulsifier/texturizer, a plasticizing/wetting agent, a filmogen, an aromatizer, a product with pharmacological activity, a product with cosmetic activity and a product with an alimentary property.

4. The film as claimed in claim 3, comprising an emulsifying or emulsifying/texturizing product selected from the group consisting of a polyoxyethylene derivative, a natural gum, a natural emulsifier, a cellulose derivative, and a starch.

5. The film as claimed in claim 3, comprising a plasticizing/wetting product selected from the group consisting of a polyol and an ester of acetic acid with glycerol.

6. The film as claimed in claim 3, comprising a filmogenic substance selected from the group consisting of a glycosamine glycan, a mucopolysaccharide, and a water-soluble polysaccharide.

7. The film as claimed in claim 1, comprising 5 to 12% of polysorbate 80.

8. The film as claimed in claim 3, comprising carob seed flour or acacia gum.

9. The film as claimed in claim 3, comprising gelatin.

10. The film as claimed in claim 3, comprising carboxymethyl cellulose or methylcellulose.

11. The film as claimed in claim 3, comprising maize starch or potato starch.

12. The film as claimed in claim 5, comprising glycerin, sorbitol or propylene glycol.

13. The film as claimed in claim 6, comprising hyaluronic acid.

14. The film as claimed in claim 6, comprising pullulan.

15. The film as claimed in claim 1, further comprising loperamide hydrochloride or melatonin.

16. The film as claimed in claim 15, comprising 15 to 45% of a combination of glycerin and sorbitol.

17. The film as claimed in claim 1, comprising 15 to 45% of a combination of glycerin and sorbitol.

18. The film as claimed in claim 1, having a thickness between 60 and 150 µm.

19. A method of treating a small wound and/or an aphtha in a subject, the method comprising providing the film as claimed in claim 1 to provide cicatizing filmogenic action for treating the small wound and/or the aphtha.

20. A method of treating a small wound and/or an aphtha in a subject, the method comprising providing the film as claimed in claim 15 to provide cicatizing filmogenic action for treating the small wound and/or the aphtha.

21. A method of treating a small wound and/or an aphtha in a subject, the method comprising providing the film as claimed in claim 16 to provide cicatizing filmogenic action for treating the small wound and/or the aphtha.

22. A method of treating a small wound and/or an aphtha in a subject, the method comprising providing the film as claimed in claim 17 to provide cicatizing filmogenic action for treating the small wound and/or the aphtha.

\* \* \* \* \*